United States Patent
Stoppenhagen et al.

(10) Patent No.: US 10,856,878 B2
(45) Date of Patent: *Dec. 8, 2020

(54) SYSTEMS AND METHODS FOR DELIVERING INTRAVASCULAR IMPLANTS

(71) Applicant: SPARTAN MICRO, INC., Fremont, CA (US)

(72) Inventors: Eric P. Stoppenhagen, Round Rock, TX (US); Mark Dias, Round Rock, TX (US)

(73) Assignee: SPARTAN MICRO, INC., Fremont, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 15/979,226

(22) Filed: May 14, 2018

(65) Prior Publication Data

US 2018/0256170 A1    Sep. 13, 2018

Related U.S. Application Data

(63) Continuation of application No. 15/825,518, filed on Nov. 29, 2017, now Pat. No. 9,968,360, which is a (Continued)

(51) Int. Cl.
*A61B 17/12* (2006.01)
*A61B 90/00* (2016.01)
*A61B 17/00* (2006.01)

(52) U.S. Cl.
CPC .... *A61B 17/12113* (2013.01); *A61B 17/1214* (2013.01); *A61B 17/12145* (2013.01);
(Continued)

(58) Field of Classification Search
CPC ........ A61B 17/12022; A61B 17/12109; A61B 17/12113; A61B 17/12118; A61B 17/1214; A61B 17/12145; A61B 2017/0046; A61B 2017/00469; A61B 2017/00477; A61B 2017/1205; A61B 2017/12054; A61B 90/39; A61B 2090/3966
See application file for complete search history.

(56) References Cited

U.S. PATENT DOCUMENTS 6,277,125 B1   8/2001  Barry et al.
6,296,622 B1  10/2001  Kurz et al.
(Continued)

FOREIGN PATENT DOCUMENTS

EP    2944278 A2   11/2015
WO  2017066386 A1   4/2017

OTHER PUBLICATIONS

U.S. Appl. No. 15/410,639, Final Office Action, dated Aug. 6, 2019, 10 pages.
(Continued)

*Primary Examiner* — Ryan J. Severson
(74) *Attorney, Agent, or Firm* — Stoel Rives LLP

(57) ABSTRACT

Systems and methods are provided for delivering and mechanically detaching embolic coils. The systems disclosed herein comprise a mechanical detachment mechanism to intravascularly release an embolic coil. The methods disclosed herein comprise a various triggering mechanisms to detach embolic coils.

16 Claims, 10 Drawing Sheets

Related U.S. Application Data continuation-in-part of application No. 15/410,639, filed on Jan. 19, 2017, now Pat. No. 10,531,876.

(60) Provisional application No. 62/343,528, filed on May 31, 2016, provisional application No. 62/343,542, filed on May 31, 2016.

(52) U.S. Cl.
CPC .... *A61B 90/39* (2016.02); *A61B 2017/00477* (2013.01); *A61B 2017/00867* (2013.01); *A61B 2017/12054* (2013.01); *A61B 2090/0811* (2016.02); *A61B 2090/3966* (2016.02)

(56) References Cited

U.S. PATENT DOCUMENTS

| | | | |
|---|---|---|---|
| 7,367,987 | B2 | 5/2008 | Balgobin et al. |
| 7,371,251 | B2 | 5/2008 | Mitelberg et al. |
| 7,371,252 | B2 | 5/2008 | Balgobin et al. |
| 7,377,932 | B2 | 5/2008 | Mitelberg et al. |
| 7,708,754 | B2 | 5/2010 | Balgobin et al. |
| 7,901,444 | B2 | 5/2011 | Slazas |
| 8,016,869 | B2 | 9/2011 | Nikolchev |
| 8,197,442 | B2 | 6/2012 | Balgobin et al. |
| 8,333,796 | B2 | 12/2012 | Tompkins et al. |
| 8,956,381 | B2 | 2/2015 | Que et al. |
| 8,974,488 | B2 | 3/2015 | Tan et al. |
| 8,998,926 | B2 | 4/2015 | Pomeranz |
| 9,579,104 | B2 | 2/2017 | Beckham et al. |
| 9,687,246 | B2 | 6/2017 | Torp |
| 9,700,322 | B2 | 7/2017 | Dias et al. |
| 9,775,621 | B2 | 10/2017 | Tompkins et al. |
| 9,968,360 | B2 * | 5/2018 | Stoppenhagen . A61B 17/12145 |
| 10,531,876 | B2 * | 1/2020 | Stoppenhagen . A61B 17/12031 |
| 2004/0220585 | A1 | 11/2004 | Nikolchev |
| 2006/0276823 | A1 | 12/2006 | Mitelberg et al. |
| 2006/0276824 | A1 | 12/2006 | Mitelberg et al. |
| 2006/0276828 | A1 | 12/2006 | Balgobin et al. |
| 2006/0276829 | A1 | 12/2006 | Balgobin et al. |
| 2006/0276830 | A1 | 12/2006 | Balgobin et al. |
| 2006/0276832 | A1 | 12/2006 | Balgobin et al. |
| 2006/0276833 | A1 | 12/2006 | Balgobin et al. |
| 2006/0276834 | A1 | 12/2006 | Balgobin et al. |
| 2007/0010849 | A1 | 1/2007 | Balgobin et al. |
| 2007/0010850 | A1 | 1/2007 | Balgobin et al. |
| 2007/0118172 | A1 | 5/2007 | Balgobin et al. |
| 2007/0239192 | A1 | 10/2007 | Litzenberg et al. |
| 2007/0239196 | A1 | 10/2007 | Pomeranz |
| 2007/0270930 | A1 | 11/2007 | Schenck |
| 2008/0045997 | A1 | 2/2008 | Balgobin et al. |
| 2008/0082176 | A1 | 4/2008 | Slazas |
| 2008/0119887 | A1 | 5/2008 | Que et al. |
| 2008/0269675 | A1 | 10/2008 | Balgobin et al. |
| 2009/0036768 | A1 | 2/2009 | Seehusen et al. |
| 2012/0041472 | A1 | 2/2012 | Tan et al. |
| 2013/0138136 | A1 | 5/2013 | Beckham et al. |
| 2014/0058434 | A1 | 2/2014 | Jones et al. |
| 2015/0112378 | A1 | 4/2015 | Torp |
| 2015/0335333 | A1 | 11/2015 | Jones et al. |
| 2017/0095259 | A1 | 4/2017 | Tompkins et al. |
| 2017/0105739 | A1 | 4/2017 | Dias et al. |
| 2017/0340330 | A1 | 11/2017 | Stoppenhagen |
| 2018/0078263 | A1 * | 3/2018 | Stoppenhagen ....... A61B 90/39 |
| 2018/0256170 | A1 * | 9/2018 | Stoppenhagen . A61B 17/12145 |

OTHER PUBLICATIONS

U.S. Appl. No. 15/410,639, Notice of Allowance, dated Oct. 17, 2019, 8 pages.

PCT/US2017/040425, International Search Report and Written Opinion, dated Sep. 15, 2017, 12 pages.

U.S. Appl. No. 15/825,518, Non-Final Office Action, dated Feb. 8, 2018, 15 pages.

U.S. Appl. No. 15/825,518, Notice of Allowance, dated Apr. 2, 2018, 7 pages.

U.S. Appl. No. 15/410,639, Non-Final Office Action, dated Feb. 21, 2019, 14 pages.

* cited by examiner

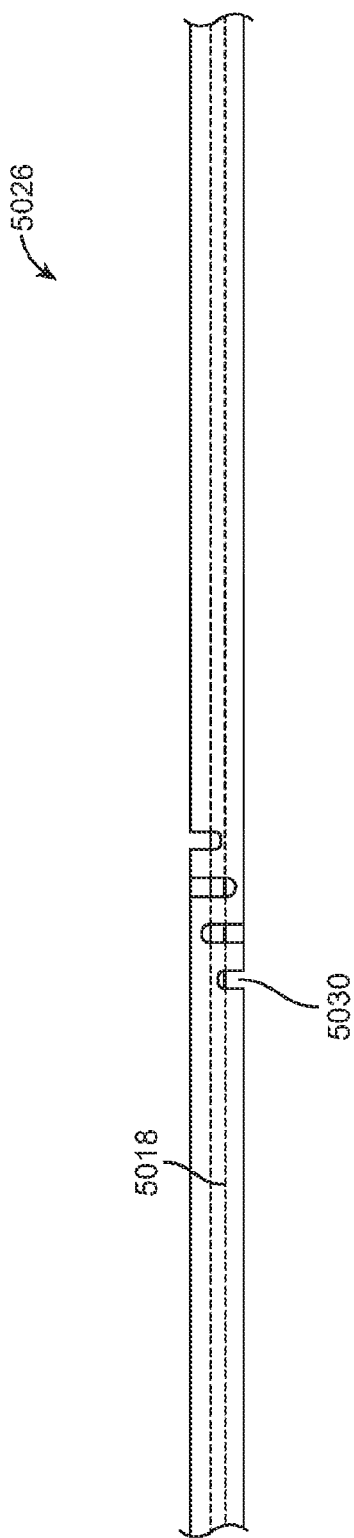

SYSTEMS AND METHODS FOR DELIVERING INTRAVASCULAR IMPLANTS

CROSS-REFERENCE

This application is a continuation of U.S. patent application Ser. No. 15/825,518, filed Nov. 29, 2017, titled "SYSTEMS AND METHODS FOR DELIVERY INTRAVASCULAR IMPLANTS", which is a continuation-in-part of U.S. patent application Ser. No. 15/410,639, filed Jan. 19, 2017, titled "SYSTEMS AND METHODS FOR DELIVERING INTRAVASCULAR IMPLANTS," which claims the benefit of U.S. Provisional Application No. 62/343,528, filed May 31, 2016, and U.S. Provisional Application No. 62/343,542, filed May 31, 2016, each of which is hereby incorporated herein by reference in its entirety.

BACKGROUND

A number of vascular disorders are treated by an intravascular delivery of an implant that is either positioned or deployed within a vessel of a body of an individual. For example, an intravascular stent used for treating peripheral artery disease may be deployed in a stenotic region of a blood vessel in order to improve blood flow past the stenosis in the vessel. For further example, an embolic coil may be placed or deployed within an intracerebral aneurysm in order to occlude the aneurysm thus preventing blood flow into the aneurysm and thus preventing a rupture of the aneurysm.

SUMMARY

Described herein are systems and methods for delivering an intravascular implant. The systems and methods described herein use an intravascular approach for delivering an implant into the intravascular system of a patient. In some embodiments of the systems and methods described herein, the systems and methods comprise a mechanical detachment system that is configured to deploy an intravascular implant, such as an embolic coil, at a target location within the vascular system of a patient when a user manually deploys the implant.

In some embodiments of the systems and methods described herein, the systems and methods are used for the delivery of an embolic coil to an intracranial aneurysm and are configured to provide manually triggered deployment of an embolic coil within the intracranial aneurysm.

The systems and methods described herein improve upon traditional implant detachment systems, such as, for example, embolic coil detachment systems, in a number of ways:

Prevention of Undesired Thrombotic Events

One example of how the systems and methods described herein improve on traditional systems and methods for delivering embolic coils is by preventing undesired thrombotic events.

Many traditional systems and methods for delivering embolic coils to cerebral aneurysms employ electrolytic detachment mechanisms, which have been shown to cause generation of gas bubbles at the detachment zone. The formation of gas bubbles intravascularly leads to the formation of blood clots, which may lead to thromboembolic complications. Furthermore, if the clot remains attached to a micro-catheter tip or to the end of an embolic coil, there is a risk that the clot will grow in size and/or embolize during repeated embolic coil detachment procedures. This presents an increased risk of the generation of blood clots which can travel to small vessels and occlude these vessels leading to anoxic injury.

Decrease in Detachment Time

Another example of how the systems and methods described herein improve on traditional systems and methods of delivering embolic coils is by decreasing the time to detach the total number of embolic coils.

The systems and methods described herein take significantly less time to detach and deploy an embolic coil as compared to traditional electrolytic systems. The systems and methods described herein comprise mechanical components that actuate rapid deployment whereas electrolytic systems require time to heat an embolic coil system in order to detach and deploy a coil. As, in most cases, delivery of multiple embolic coils into one cerebral aneurysm is often necessary, the reduction in procedure time by the systems and methods described herein presents a significant advantage.

Prevention of Detachment Failure

Yet another example of how the systems and methods described herein improve on traditional systems and methods of delivering embolic coils is by preventing a failed detachment of an embolic coil.

Traditional electrolytic detachment systems and methods have been shown to have a significant detachment failure rate. Detachment failure may occur due to electrical equipment failure and/or failure to properly induce a current through the device and the patient. Because the systems and methods described herein employ mechanical components rather than electrical components, the failure rate is significantly lower than that of the traditional electrolytic deployment systems.

Described herein is an embolic coil delivery system for delivering and deploying an embolic coil at an aneurysm comprising:
  i. a conduit having a deployment location from which the embolic coil is deployed and a first radiopaque marker;
  ii. a detachment system configured to fit within the conduit and to be slideably advanced and withdrawn within the conduit, the detachment system comprising:
    a. a detachment mechanism comprising:
      1) a tab comprising a memory material and having a first position and a second position, wherein the memory material is configured to move the tab from the first position to the second position;
      2) a primary member configured and positioned to engage with the tab so that the tab is in the first position when engaged with the primary member and is moved to the second position by the memory material when the primary member is no longer engaged with the tab;
      3) an anchoring element coupled to the embolic coil and configured and positioned to engage with the tab in the first position so that the embolic coil is coupled to the detachment system when the tab is in the first position, and wherein the anchoring mechanism is configured and positioned to not engage with the tab in the second position so that the embolic coil is deployed when the tab is in the second position;

4) a radiopaque marker coupler;
b. a second radiopaque marker that is mechanically coupled with the radiopaque marker coupler and is positioned to align with the first radiopaque marker when the detachment mechanism is positioned at the deployment location.

In some embodiments of the delivery system, the detachment system comprises a flexible tube that surrounds the detachment system and fixedly couples the radiopaque marker coupler and the radiopaque marker. In some embodiments of the delivery system, the first radiopaque marker partially surrounds the conduit so that when the detachment mechanism is advanced within the conduit and the first radiopaque marker aligns with the second radiopaque marker, the second radiopaque marker is radiographically visible. In some embodiments of the delivery system, the tab comprises a memory metal material. In some embodiments of the delivery system, the detachment mechanism further comprises a primary member that detachably couples with the tab so that when the primary member and the tab are coupled, the tab is in the first position and when the primary member and the tab are decoupled, the tab moves to the second position. In some embodiments of the delivery system, the tab moves to the second position when the primary member is drawn away from the tab. In some embodiments of the delivery system, the detachment system includes a segment that is configured to manually detach from the detachment system, and wherein the primary member is coupled to the segment so that when the segment is manually detached and withdrawn away from the detachment system, the primary member is drawn away from the tab so that the tab moves to the second position and deploys the coil. In some embodiments of the delivery system, the segment comprises oblong cuts around its outer diameter that are configured to fracture the segment when a bending force is applied to the segment. In some embodiments of the delivery system, the primary member is coupled with a hand-held detachment device configured to clamp the primary member such that the primary member is drawn away from the tab when the grip is drawn away from the conduit, and wherein the grip comprises a viewing window that shows when the primary member is drawn away from the tab.

Also described herein is a method for deploying an embolic coil in an intracranial aneurysm comprising: directing a conduit through one or more blood vessels of the patient to the aneurysm, the conduit comprising a first radiopaque marker and a deployment location; advancing a detachment system through the conduit while the conduit is within the blood vessel, the detachment system comprising a radiopaque marker coupler, a second radiopaque marker, and a detachment mechanism comprising a tab having a first position and a second position; deploying the embolic coil within the aneurysm using the detachment system; wherein the radiopaque marker coupler and the second radiopaque marker couple mechanically; wherein when the detachment mechanism is positioned at the deployment location, the first radiopaque marker and the second radiopaque marker align; wherein the embolic coil is coupled to an anchoring element; wherein when the tab is in the first positon, the anchoring element engages the tab thus coupling the embolic coil to the detachment system; and wherein the anchoring element does not engage the tab in the second position thus decoupling the embolic coil from the detachment system and thus deploying the embolic coil in the intracranial aneurysm. In some embodiments of the method, the detachment system comprises a flexible tube that surrounds the detachment system and fixedly couples the radiopaque marker coupler and the radiopaque marker. In some embodiments of the method, the first radiopaque marker partially surrounds the conduit so that when the detachment system is advanced within the conduit and the first radiopaque marker aligns with the second radiopaque marker, the second radiopaque marker is radiographically visible. In some embodiments of the method, the tab comprises a memory metal material. In some embodiments of the method, the detachment mechanism further comprises a primary member that detachably couples with the tab so that when the primary member and the tab are coupled, the tab is in the first position, and when the primary member and the tab are decoupled, the tab moves to the second position. In some embodiments of the method, the step of deploying comprises decoupling the primary member from the tab by drawing the primary member away from the tab. In some embodiments of the method, the conduit includes a segment that is configured to manually detach from the conduit, and wherein the primary member is coupled to the segment so that when the segment is manually detached and withdrawn away from the conduit, the primary member is drawn away from the tab so that the tab moves to the second position and deploys the embolic coil. In some embodiments of the method, the segment comprises oblong cuts around its outer diameter that are configured to fracture the segment when a bending force is applied to the segment. In some embodiments of the method, the primary member is coupled with a hand-held detachment device configured to clamp the primary member such that the primary member is drawn away from the tab when the grip is drawn away from the conduit, and wherein the grip comprises a viewing window that shows when the primary member is drawn away from the tab.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 5 shows an exemplary illustration of an embodiment of an expansion tube.

DETAILED DESCRIPTION

Described herein are systems and methods for delivering and deploying an intravascular implant to an intravascular target such as, for example, delivering one or more embolic coils to an intracranial aneurysm and deploying the one or more embolic coils within the aneurysm.

Figure 1:
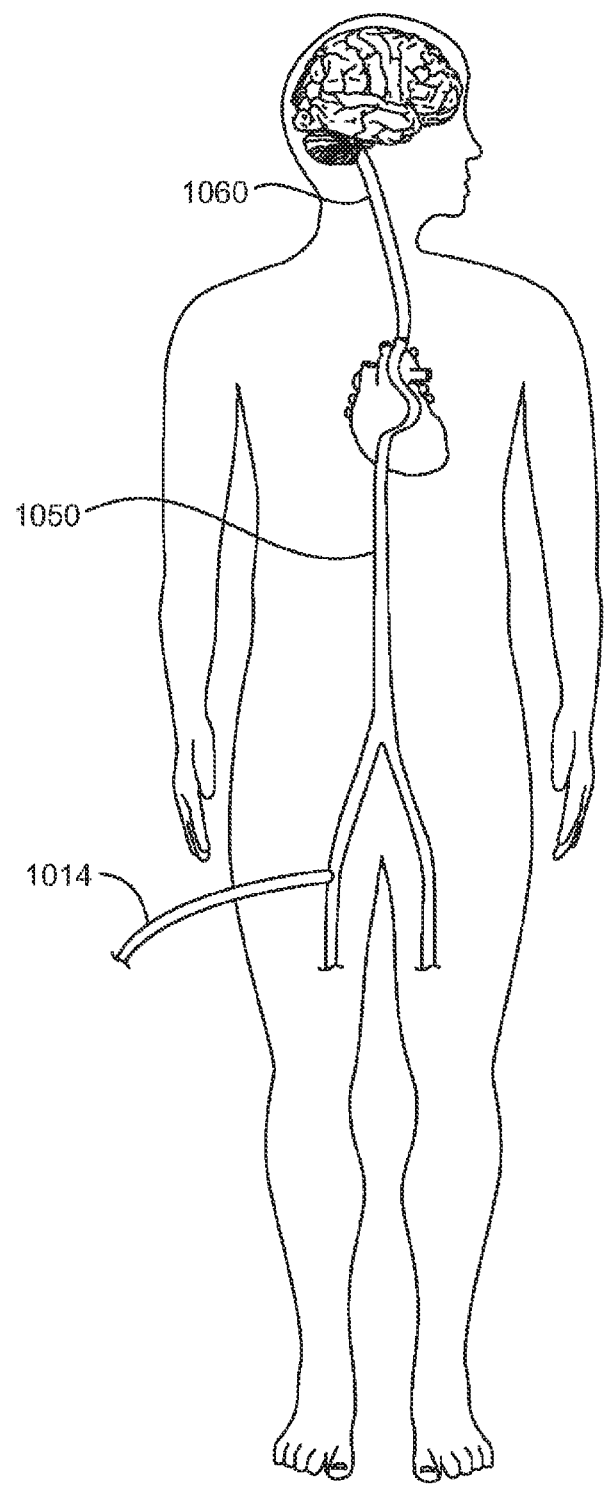
FIG. 1 shows an illustration of the anatomical path of travel of a delivery system.

A delivery system as described herein comprises a conduit such as a traditional catheter or micro-catheter and a detachment system that is configured to be slideably advanced within the catheter. The catheter of the delivery system described herein is configured to be advanced through a blood vessel of a patient to a target location. For example, FIG. 1 shows an illustration of the anatomical path of travel of a catheter 1014. The catheter 1014 may be inserted into a femoral artery of a patient (using, for example, Seldinger technique) and advanced up through the aorta 1050 of the patient, from there the catheter may be advanced up through a carotid artery 1060 to an intracranial target location such as an intracranial aneurysm where an intravascular implant may be deployed in order to, for example, occlude the aneurysm thus preventing aneurysm rupture. The conduit of the delivery system is thus configured to deliver the detachment system described herein to a target location. In some embodiments, the delivery system as described herein does not include a conduit, but rather the detachment system is delivered directly to a target location.

Delivery System

Figure 2:
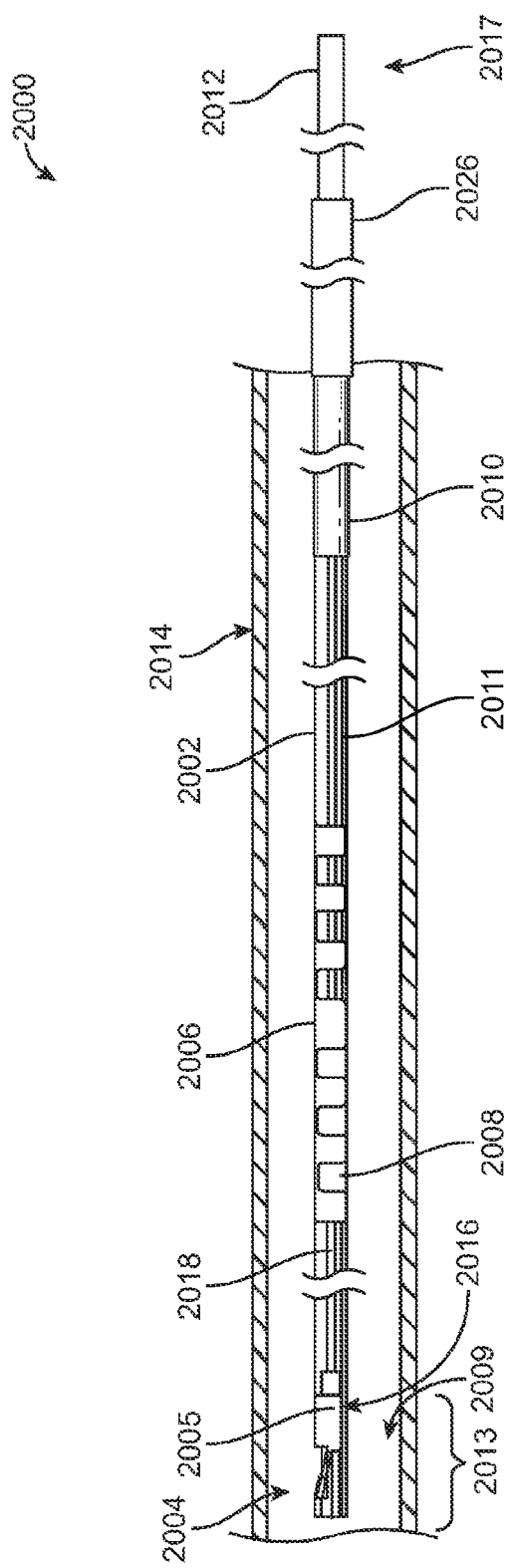
FIG. 2 shows an illustration of an exemplary embodiment of a delivery system for delivering and deploying an intravascular implant such as an embolic coil.

FIG. 2 shows an illustration of an exemplary embodiment of a delivery system 2000 for delivering and deploying an intravascular implant (not shown) such as an embolic coil. Other non-limiting examples of implants suitable for use with the systems, devices, and methods described herein include, for example, occluding coils and intravascular stents.

A delivery system 2000 comprises a conduit such as a standard catheter 2014 or micro-catheter (or other conduit) and a detachment system 2004. In the exemplary embodiment shown in FIG. 2, the conduit of the delivery system 2000 comprises a catheter 2014. The detachment system 2004 comprises an elongate body that is configured to be slideably positioned (i.e. advanced and withdrawn) within the catheter 2014 and, in some embodiments, the detachment system 2004 is delivered via the catheter 2014 to a target location such as, for example, an intracranial aneurysm. That is, in embodiments of the delivery system that include a catheter 2014, the catheter 2014 with the detachment system 2004 within it is typically delivered to a target location by a user, wherein a target location may comprise, for example, an intracranial aneurysm or, for example, an atherosclerotic lesion. In other embodiments, the detachment system 2004 is delivered directly to a target location.

Detachment System

The detachment system 2004 comprises a proximal end 2017 and a distal end 2016, which are each configured to include different functional elements of the detachment system 2004. In general, the proximal end 2017 of the detachment system 2004 remains outside of the patient during the use of the delivery system 2000, and the proximal end 2017 of the detachment system 2004 generally includes features that allow a user to manually direct the detachment system 2004 and control the deployment of an implant. The proximal end 2017 of the detachment system 2004 is configured to provide a mechanism for manually deploying an implant at a target location by a user of the delivery system 2000. In general, the distal end 2016 includes a detachment mechanism 2005 that is configured to release or deploy an intravascular implant at a target location and a radiopaque marker 2006 that is positioned to align with a radiopaque marker on the distal end of the catheter 2014 when the detachment system 2004 is within a proper position relative to the catheter 2014 for implant deployment.

Detachment system 2004 comprises a detachment mechanism 2005 at its distal end 2016. In some embodiments of the delivery system 2000, the detachment system 2004 comprises a detachment mechanism and forms an elongate body comprising a series of respectively optional interconnected tubes comprising an optional shrink tube 2002, an optional connecting tube 2010, an optional expansion tube 2026, and an optional grip tube 2012. The optional interconnected tubes 2002, 2010, and 2026, and 2012 are each respectively configured to provide different qualities or features to the detachment system 2004. A shrink tube 2002 comprises a flexible material such as a polymer, and is configured to cover and/or surround at least a portion of the distal end 2016 of the detachment system 2000 while providing flexibility to maneuver through bends in the vasculature system. The shrink tube 2002 also maintains a tight coupling between the radiopaque marker 2006 and the detachment mechanism 2005 via mechanical coupling between the radiopaque marker 2006 and a radiopaque marker coupler 2008. A connecting tube 2010 may optionally be connected to the shrink tube 2002 and comprises a relatively rigid material (as compared to the shrink tube 2002) that provides rigidity to portions of the distal 2016 end and/or proximal end 2017 so that the detachment system 2004 is more easily advanced and withdrawn within the catheter 2014. An expansion tube 2026 is optionally connected to the connecting tube 2010, and provides a segment with an expanded diameter (as compared to the optional shrink tube 2002 and connecting tube 2010) providing ease of handling relative to the relatively small diameter optional shrink tube 2002 and connecting tube 2010. In some embodiments of the detachment system 2004, and expansion tube 2026 facilitates deployment of an implant from the detachment mechanism 2005 by facilitating manual withdrawal of a primary member 2018. An optional grip tube 2012 provides a hand grip for a user, and in some embodiments of the detachment system 2004 it is replaced by a hand-held detachment device. A connecting wire 2011 connects the distal portion of the detachment system.

In some embodiments of the delivery system 2000, a detachment mechanism 2005 entirely comprises a memory metal material such as, for example, nitinol. In some embodiments of the detachments system 2004, only the detachment mechanism 2005 comprises a memory metal material such as nitinol. In some embodiments of the detachment mechanism 2005, the detachment mechanism 2005, not including the primary member 2018 (which comprises a different material), comprises a memory material such as nitinol. In some embodiments of the detachment mechanism 2005, the detachment mechanism 2005, not including the radiopaque marker 2006 (which comprises a different material), comprises a memory material such as nitinol. In some embodiments of the detachment mechanism 2005, the detachment mechanism 2005, not including the primary member 2018 and the radiopaque marker 2006 (which comprise a different material), comprises a memory material such as nitinol.

The distal end of the detachment system 2004 includes a radiopaque marker 2008, and the distal end of the catheter 2014 includes a radiopaque marker (not shown). Non-limiting examples of metals suitable for use as either the radiopaque marker 2008 of the detachment system 2004 or the radiopaque marker on the catheter include noble metals or alloys such as platinum, platinum-tungsten, platinum iridium, silver, or gold. In some embodiments of the delivery system 2000, the radiopaque marker 2008 of the detachment system 2004 and the radiopaque marker on the catheter 2014 are positioned so that they align with one another so when a detachment mechanism 2005 is positioned at a deployment location 2009. In some embodiments of the delivery system 2000, the radiopaque marker 2008 of the detachment system 2004 and the radiopaque marker of the catheter 2014 are positioned so that they align at a location about 30 mm proximal to the deployment location 2009.

In some embodiments of the delivery system 2000, a detachment system 2004 includes a radiopaque marker coupler 2008 at a radiopaque marker location. The radiopaque marker coupler 2008 is a portion of the detachment system 2004 that is configured to couple with a radiopaque marker 2006. That is, a radiopaque marker 2008 of the detachment system 2004 typically comprises a metal such as, for example, platinum, platinum-tungsten, platinum iridium, silver, or gold. Because the remaining portions of the detachment mechanism 2005 (except in some embodiments the primary member 2018 is not) comprise a memory material such as nitinol, coupling the radiopaque marker 2008 to the detachment mechanism 2005 is not easily achievable with typical methods such as welding due to differences between the materials (i.e. between the radiopaque marker 2008 and the memory material of the detachment mechanism 2005). As such, a radiopaque marker coupler 2008 is configured to couple with a radiopaque marker 2006 mechanically without the need for the two elements to be welded or similarly fused. In some embodiments of the detachment system 2004, a radiopaque marker coupler 2008 have complimentary shapes that are configured so that the two components couple together by fitting together as shown in FIG. 2. That is, in some embodiments of the detachment system 2004, a radiopaque marker coupler 2008 is a component of the detachment mechanism 2005 that has an alternating tooth pattern (as shown) with elevations and indentations or alternatively, for example, a saw-tooth pattern, and likewise the radiopaque marker 2009 has a complimentary alternating tooth pattern (as shown) with elevations and indentations or alternatively, for example, a saw-tooth pattern so that the two components, the radiopaque marker coupler 2008 and the radiopaque marker coupler 2009, fit together wherein an elevation of one component fits an indentation of the complimentary component. In some embodiments of the detachments system 2004, a flexible shrink tube 2002 tightly surrounds these two coupled components, the radiopaque marker coupler 2008 and the radiopaque marker coupler 2009, so that they are fixedly coupled together.

In order for the detachment system 2004 to properly deploy an implant such as an embolic coil within an aneurysm (i.e. the target), the detachment mechanism 2005 must be advanced to a deployment location 2013 along the catheter 2014. The deployment location 2013 may be a different location along the catheter 2014 depending on the type of implant deployed. For example, in some embodiments of the delivery system 2000, for proper deployment of an embolic coil or other implant within an aneurysm or other target location, the embolic coil or other implant is advanced entirely out of the aperture 2009 of the catheter 2014. For example, in some embodiments of the delivery system 2000, for proper deployment of an embolic coil or other implant within an aneurysm or other target location, the embolic coil is advanced partially out of the aperture 2009 of the catheter 2014. For example, in some embodiments of the delivery system 2000, for proper deployment of an embolic coil or other implant within an aneurysm or other target location, the detachment mechanism is advanced entirely out of the aperture 2009 of the catheter 2014. In some embodiments of the delivery system 2000, for proper deployment of an embolic coil or other implant within an aneurysm or other target location, the detachment mechanism 2005 is advanced partially out of the aperture 2009 of the catheter. As shown in the exemplary embodiment shown in FIG. 2, a detachment mechanism 2005 in the illustrated embodiment, is positioned within the distal portion of the catheter 2014 for proper deployment of an implant and as such the deployment location 2013 in the embodiment shown in FIG. 2 is located at the distal end of the catheter 2014.

That is, as shown in FIG. 2, the distal end 2016 of the catheter defines a deployment location 2013, which is a position or zone to where the detachment system 2004 (and thus the detachment mechanism 2005 at the distal end of the detachment system) must be advanced in order to achieve successful deployment of an implant. For example, in embodiments of the delivery system wherein the detachment system 2004 remains entirely within the distal end of the catheter 2014 in order to achieve proper deployment of an implant, the deployment location 2013 is located where the detachment system 2004 is positioned within the distal end 2016 of the catheter. For example, in embodiments of the delivery system wherein the detachment system 2004 is partially out of the aperture 2009 at the distal end 2016 of the catheter and partially within the distal end 2016 of the catheter in order to achieve proper deployment of an implant, the deployment location is located partially outside of the aperture 2009 and partially within the catheter where the detachment system 2004 is positioned. For example, in embodiments of the delivery system wherein the detachment system 2004 is completely out of the aperture 2009 in order to achieve proper deployment of an implant, the deployment location is located where the detachment system 2004 is positioned outside of the catheter.

In general, the proximal end 2017 of catheter 2002 is coupled to one or more features that provide a user with manual control over the advance of the implant to the target and deployment of the implant at or in the target. In some embodiments of the delivery system 2000, the proximal end 2017 of the catheter 2002 is coupled with an expansion tube 2026. The expansion tube 2026 is configured to have a larger diameter than the relatively small diameter of the microcatheter 2002. The expansion tube 2026 is generally configured so that it may couple the delivery system 2000 to other elements. For example, in some embodiments of the delivery system 2000, the expansion tube 2026 couples to a grip tube 2012 at the most proximal end 2017 of the delivery system 2000. The grip tube 2012 provides a user with a manual grip to advance and/or withdraw the detachment system in order to guide the detachment system through the vasculature of a patient. In some embodiments of the delivery system 2000, the expansion tube 2026 includes one or more oblong cuts or breaks within its material in order to facilitate a manual fracturing of the expansion tube 2026 so that the expansion tube 2026 is divided. Manually dividing the expansion tube 2026 provides a mechanism for withdrawing the fractured portion of the expansion tube 2026 away from the detachment system in a proximal direction, which is used in some embodiments of the delivery system 2000 to manually trigger deployment of an implant. In some embodiments of the delivery system 2000, the expansion tube 2026 couples with an external detachment device that is configured to manually trigger deployment of an implant using the detachment system 2004

Detachment Mechanism

In some embodiments of the systems, devices, and methods described herein, a detachment mechanism 2005 is positioned at the distal end 2016 of the detachment system 2004, and the detachment system 2004 along with the catheter 2014 form the delivery system 2000.

In some embodiments, a detachment mechanism 2005 comprises a primary member 2018, an anchoring member, and a tab, which are configured and positioned to actuate the detachment mechanism 2005 causing the release and/or deployment of an intravascular implant.

A primary member 2018 as shown in FIG. 2 is configured in some embodiments so that it is long enough to extend the length of the delivery system 2000 when the deployment mechanism 2005 is at the deployment location 2009.

Figure 3:
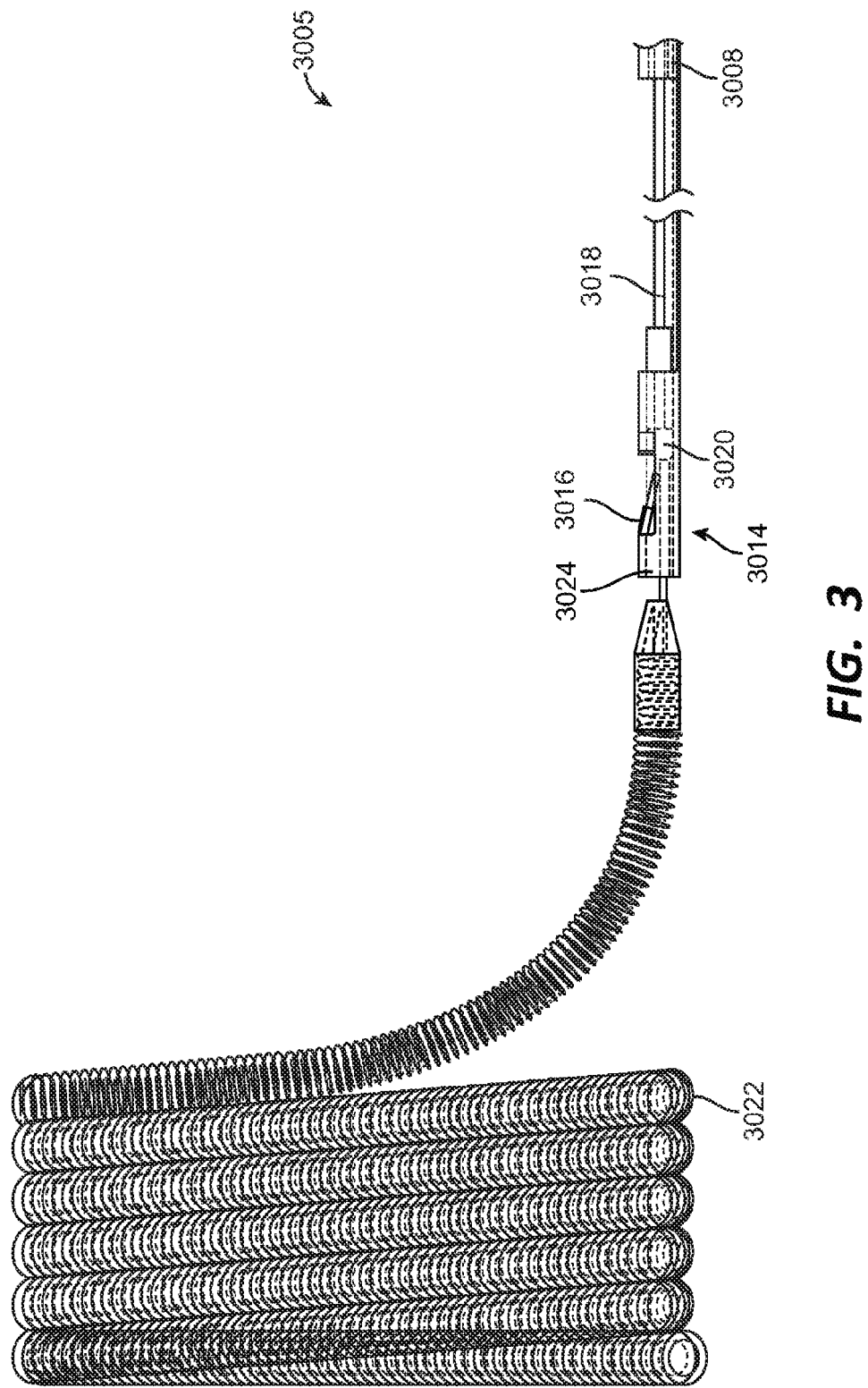
FIG. 3 shows an illustration of an exemplary embodiment of a detachment system which comprises an embolic coil that is detachably coupled to the detachment system.

A number of additional features of embodiments of the detachment mechanism 2005 are now described with additional reference to FIG. 3 as well as further reference to FIG. 2:

FIG. 3 shows an illustration of an exemplary embodiment of a detachment mechanism 3005 which comprises an embolic coil 3022 (or other implant) that is detachably coupled to the detachment mechanism 3005.

The detachment mechanism 3005 comprises elements that are configured to cause the deployment of an intravascular implant 3022. In some embodiments, the detachment mechanism 3005 includes a tab 3016, an optional primary member 3018, and an optional anchoring element 3020.

Tab 3016 of a detachment mechanism 3005 is parallel to the axis of the conduit, and is configured to have at least two configurations or positions, at least a first configuration or position and a second configuration or position. In a first configuration or position of the tab 3016, an embolic coil 3022 is held or coupled with the tab 3016, and in a second configuration or position of the tab 3016 releases or decouples from an embolic coil 3022. In some embodiments of detachment system, a tab 3016 is either a portion of or integral with a housing 3024. In some embodiments of the delivery system 3000, a tab 3016 comprises a memory metal or other memory material such as nitinol. A housing 3024 is configured to contain at least a portion of an embolic coil 3022 and, in some embodiments, an anchoring element 3020 that is coupled with the embolic coil 3022.

In some embodiments of the detachment mechanism 3005, a tab 3016 of a detachment mechanism 3005 detachably couples with a distal portion of a primary member 3018. In these embodiments, while coupled with the primary member 3018, the tab 3016 is in a first position wherein the tab 3016 is depressed or deflected towards the interior of the housing 3024. When the tab 3016 is deflected towards the interior of the housing 3024 in its first position, it is positioned to couple directly with either an embolic coil 3022 that is at least partially within the housing 3024 or, in some embodiments, couple indirectly with an embolic coil 3022 by coupling with an anchoring element 3020 that in some embodiments is coupled with an embolic coil 3022. When the primary member 3018 is engaged with the tab 3016, the tab 3016 may be deflected along a hinge and extend into the interior of the housing 3024. The hinge is perpendicular with an axis of the conduit. By virtue of coupling to the tab 3016 in its first position, the embolic coil 3022 is held within the housing 3024 of the detachment system 3016.

In some embodiments of the detachment mechanism 3005, an embolic coil 3022 (or other intravascular implant) is coupled with an anchoring element 3020 that is configured to couple with a tab 3016. In these embodiments, an anchoring element is configured to releasably couple with a tab 3016 when the tab 3016 is in the first position and deflected towards the interior of the housing. For example, in some embodiments of the delivery system 3000, as shown in FIG. 3, an anchoring element 3020 comprises a sphere or ball and when the tab 3016 is in its first position, it hooks or latches the ball 3020 so that the ball 3020 is held within the housing 3024 and thus the embolic coil 3022 is held by the detachment mechanism 3014.

In embodiments of the detachment mechanism 3005 that include a primary member 3018, when the primary member is coupled with the tab 3016 it holds the tab 3016 in the first position of the tab 3016 so that the tab 3016 is deflected towards the interior of the housing 3024. When the primary member 3018, in these embodiments, is decoupled from the tab by being, for example, withdrawn in a proximal direction, the tab 3016 moves away from the interior of the housing 3024 to move to a second position. In embodiments where the tab 3016 comprises a memory material, the material of the tab 3016 facilitates its movement away from the interior of the housing 3024 when decoupled from the primary member 3018. In some embodiments of the system 3000, a primary member is withdrawn proximally by a user when the detachment system is positioned near a target location such as, for example, an intracranial aneurysm. A primary member 3018 may, for example, comprise a wire that extends out of the proximal end 3017 of the catheter 3002 to a location where the wire may be pulled proximally by a user thus decoupling the primary member 3018 and the tab 3016.

In some embodiments of the detachment system 3004, an expansion tube 3026 is configured to fracture so that at least a portion of the expansion tube 3026 may be withdrawn in a proximal direction away from the rest of the detachment system. In some of these embodiments, a primary member 3018 is coupled with an expansion tube 3026 so that when the expansion tube 3026 is fractured and withdrawn in a proximal direction, the primary member 3018 is decoupled from the tab 3016 so that the tab 3016 moves from the first position to the second position and causes the release of the embolic coil 3022. In some embodiments of the delivery system 3000, a primary member 3018 comprises a wire that spans the length of the detachment system and extends out to a hand-held detachment device. In these embodiments, the hand-held detachment device includes a manually operated clamp that is configured to grip the primary member 3018 and withdraw it in a proximal direction thus decoupling the primary member 3018 from the tab 3016 so that the tab 3016 moves from the first position to the second position and causes the release of the embolic coil 3022.

Figure 4:
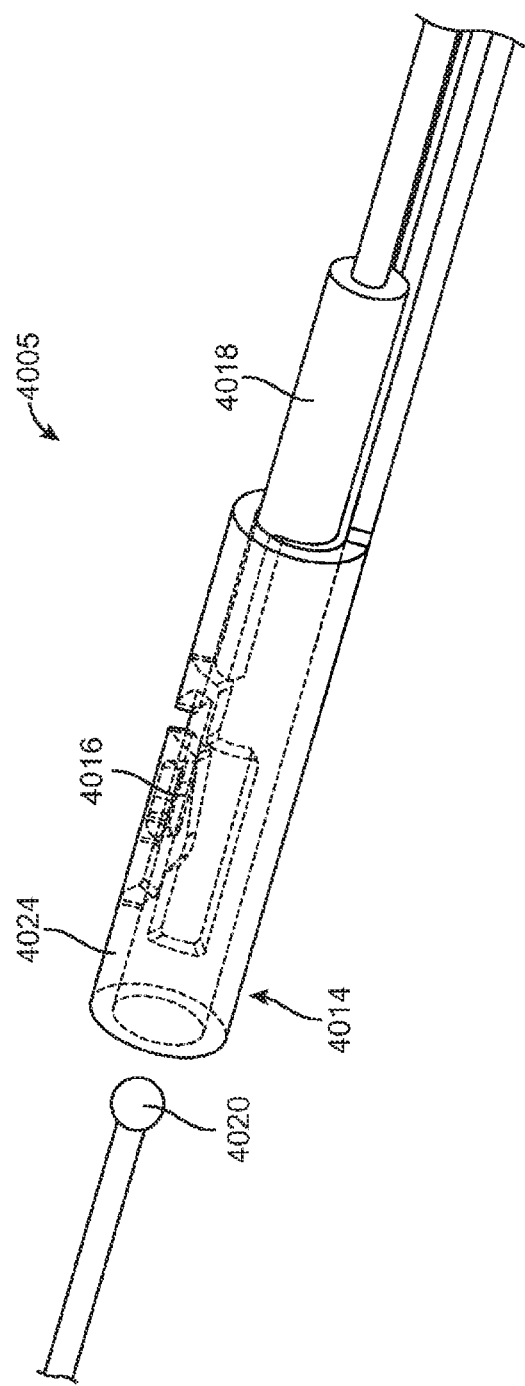
FIG. 4 shows an illustration of an embodiment of a distal end of a detachment system as an embolic coil is deployed from a detachment system.

FIG. 4 shows an illustration of an embodiment of a distal end of a detachment mechanism 4005 showing how an intravascular implant is deployed from a detachment system 4014. As described with reference to FIG. 2, a tab 4016 has at least a first position and a second position. In the second position of a tab 4016, the tab 4016, as shown in FIG. 4, is positioned so that it is not deflected towards the interior of a housing 4024 but rather positioned away from the interior of the housing 4024. Primary member 4018 is shown being withdrawn away from and thus decoupled from the tab 4016. As such, an anchoring element 4020 is no longer held by the detachment system 4014 and an embolic coil (not shown in FIG. 4) is released or deployed at a target location.

Figure 9:
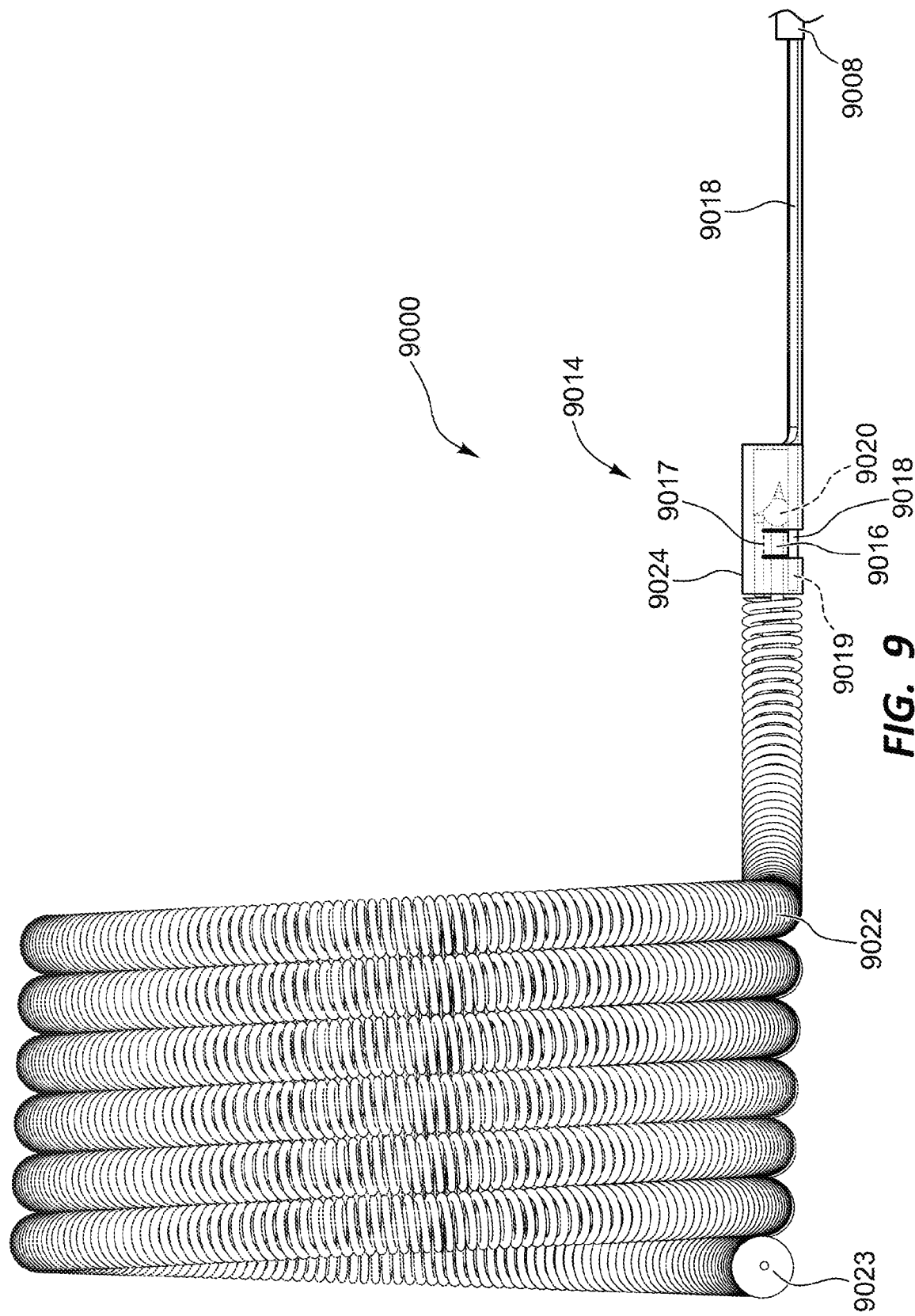
FIG. 9 shows an illustration of an exemplary embodiment of a detachment system which comprises an embolic coil that is detachably coupled to the detachment system.

FIG. 9 illustrates an alternative embodiment of a detachment system 9000 which comprises an embolic coil 9022 (or other implant) that is detachably coupled to an detachment mechanism 9014.

The detachment mechanism 9014 comprises elements that are configured to cause the deployment of an intravascular implant 9022. In some embodiments, the detachment mechanism 9000 includes a tab 9016, a primary member 9018, and an anchoring element 9020.

Tab 9016 of detachment mechanism 9014 is perpendicular to the axis of the conduit, and is configured to have at least two configurations or positions, at least a first configuration or position and a second configuration or position. In a first configuration, the embolic coil 9022 is coupled with the tab 9016, and in a second configuration, the embolic coil 9022 is released or decoupled from the detachment mechanism 9014. In some embodiments of detachment mechanism 9014, the tab 9016 is either a portion of or integral with a housing 9024. In some embodiments of the delivery system 9000, the tab 9016 comprises a memory metal or other memory material such as nitinol. The housing 9024 is configured to contain at a least a portion of embolic coil 9022 and, in some embodiments, an anchoring element 9020 is coupled with the embolic coil 9022.

In some embodiments of the detachment mechanism 9014, the tab 9016 may be held in the first configuration or position by a primary member 9018. Primary member 9018 may engage with an upper surface of the tab 9016 and the primary member 9018 extends along the width of the tab 9016. The primary member 9018 may also engage with the inner surface of the housing 9024 on opposing ends of the tab 9016. For example, a distal end 9019 may engage with the inner surface of the housing 9024 on the distal end of the housing 9024. When the primary member 9018 is engaged with the tab 9016, the tab 9016 may be deflected along a hinge 9017 and extend into the interior of the housing 9024. The hinge 9017 is parallel with an axis of the conduit. The portion of primary member 9018 that is proximal of the distal end 9019 of the primary member 9018 engages with the upper portion of the tab 9018 and is exposed when the tab 9016 is in the first configuration. By virtue of the primary member 9018 deflecting the tab 9016 into the interior of the housing 9024 and placing the tab 9016 in the first configuration or position, the embolic coil 9022 is held within the housing 9024 of the detachment system 9000.

In some embodiments of the detachment mechanism 9014, the embolic coil 9022 (or other intravascular implant) is coupled with an anchoring element 9020 that is configured to engage with the tab 9016. In these embodiment, the anchoring element 9020 is configured to releasably couple with the tab 9016 when the tab 9016 is in the first position and deflected towards the interior of the housing 9024. For example, in some embodiments of the delivery system 9000, as shown in FIG. 9, the anchoring element 9020 may be a sphere or ball and when the tab 9016 is in its first position, it hooks or latches the ball 9020 so that the ball is held within the housing 9024 and thus the embolic coil 9022 is held by the detachment mechanism 9014.

In some embodiments, when the primary member 9018 is engaged with the tab 9016 it holds the tab 9016 in the first position so that the tab 9016 is deflected towards the interior of the housing 9024. When the primary member 9018, in these embodiments, is disengaged from the tab 9016 by being, for example, withdrawn in a proximal direction, the tab 9016 moves away from the interior of the housing 9024 to move to a second position. In embodiments, where the tab 9016 comprises a memory material, the material of the tab 9016 facilitates its movement away from the interior of the housing 9024 when disengaged from the primary member 9018. In some embodiments of the detachment system 9000, a primary member is withdrawn proximally by a user when the detachment system 9000 is positioned near a target location such as, for example, an intracranial aneurysm.

Figure 10A:
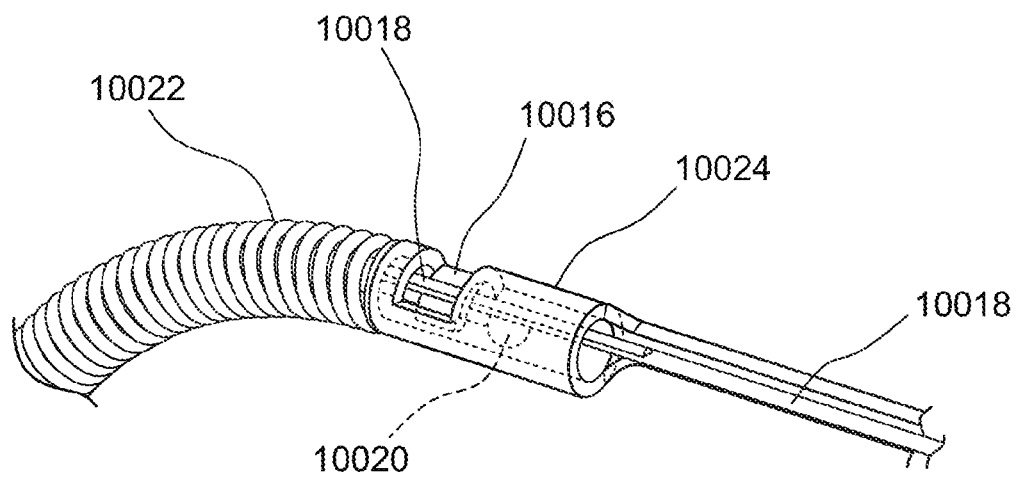
FIG. 10A shows an illustration of an embodiment of a distal end of the detachment system of FIG. 9, with the embolic coil coupled to the detachment system.

FIG. 10A is a detailed view of FIG. 9 in which the embolic coil 10022 is coupled to the detachment mechanism 10014. The tab 10016 is held in the first position by the primary member 10018 and the anchoring element 10020 is secured to the detachment mechanism 10014 by the tab 10016.

Figure 10B:
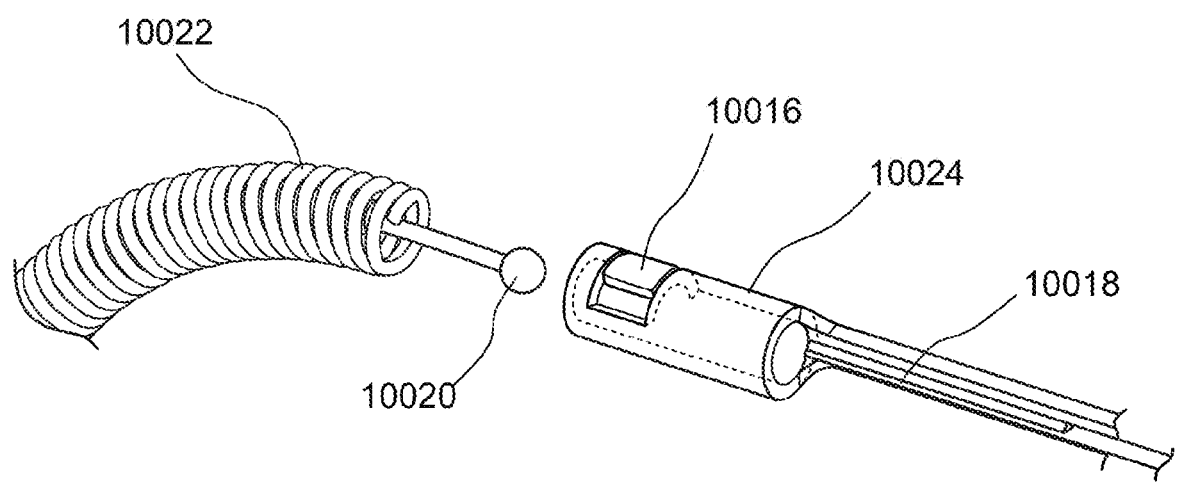
FIG. 10B shows an illustration of an embodiment of a distal end of the detachment system of FIG. 9 as the embolic coil is deployed from the detachment system.

FIG. 10B is a detailed view of the embolic coil 10022 released from the detachment mechanism 10014. The primary member 10018 has been withdrawn in the proximal direction and the tab 10016 has moved from the first position to the second position and the anchoring element 10020 is released from the detachment mechanism 10014. When the anchoring element 10020 is released from the detachment mechanism 10014, the embolic coil may be deployed at the target position, such as, for example, an intracranial aneurysm.

In some embodiment, the distal end of the embolic coil 9022 includes a radiopaque marker 9023. Non-limiting examples of metals suitable for use as radiopaque marker include noble metals or alloys such as platinum, platinum tungsten, platinum iridium, silver, or gold. The deployment system 9000 may further include additional radiopaque markers as discussed in regard to FIG. 2, such as a radiopaque marker at the distal end of the detachment system and a radiopaque marker at the distal end of the catheter. In addition, some embodiments may include a radiopaque marker coupler as discussed in regard to FIG. 2. The radiopaque marker 9023 on the distal end of the embolic coil 9022 may be used to determine when the embolic coil 9022 has been deployed by the deployment mechanism 9014. A user may determine when the embolic coil 9022 has been deployed by comparing the position of the radiopaque marker 9023 with the positions of the first and second radiopaque markers. As the first and second radiopaque markers move away from radiopaque marker 9023, the user may know that the embolic coil has been deployed.

Expansion Tube

FIG. 5 shows an exemplary illustration of an embodiment of an expansion tube 5026. As described with reference to FIGS. 1 and 2, some embodiments of detachment system include an expansion tube 5026 at the proximal end 2017 of the system. In some of these embodiments, an expansion tube 5026 includes one or more cuts 5030 at least partially surrounding the diameter of the expansion tube 5026 so that the cuts 5030 are positioned and/or configured to facilitate a fracture of the expansion tube 5026 when a bend is applied to the expansion tube 5026 by a user. Also shown in FIG. 5 is a primary member 5018 within the expansion tube 5026. In some embodiments of the delivery system 2000, an expansion tube 5026 may be further coupled at its proximal end 2017 to a hand-grip (not shown in FIG. 5) that is configured to allow a user to control the advancement and withdrawal of the catheter as well as control over the manual deployment of an implant. As described with reference to FIGS. 1-2, a primary member 5018, in some embodiments of detachment system, is connected to either an expansion tube 5026 or a hand-grip. When the expansion tube 5026 is fractured, the fractured portion of the expansion tube 5026 (and some embodiments along with a hand-grip) is able to be withdrawn away from the catheter in a proximal direction. In some embodiments of detachment system, when the expansion tube 5026 is fractured so that detachment system separates into a distal piece and a proximal piece that are able to be withdrawn from one another, the primary member 5016 is no longer held against the tab 2016, so that the tab moves to a second position (facilitated by the memory material), which exerts a force on the primary member 5016 driving it proximally.

Hand-Held Detachment Device

Figure 6A:
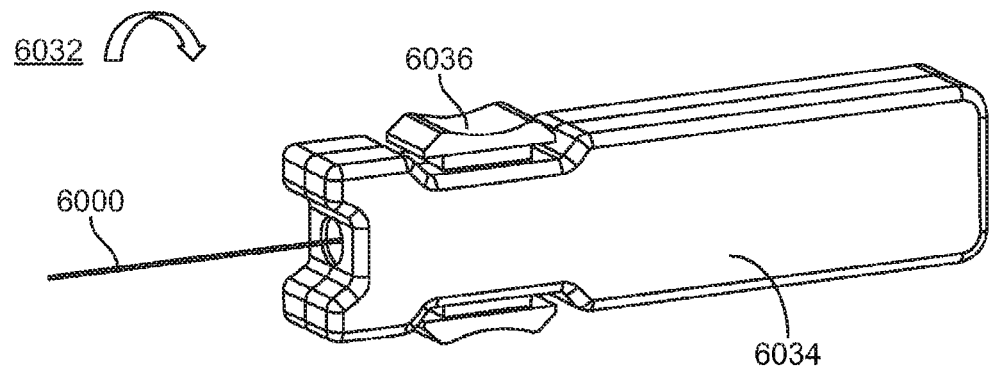
FIGS. 6A-6B show an illustration of a mechanism for manually deploying an intravascular implant using a hand-held detachment device.
Figure 6B:
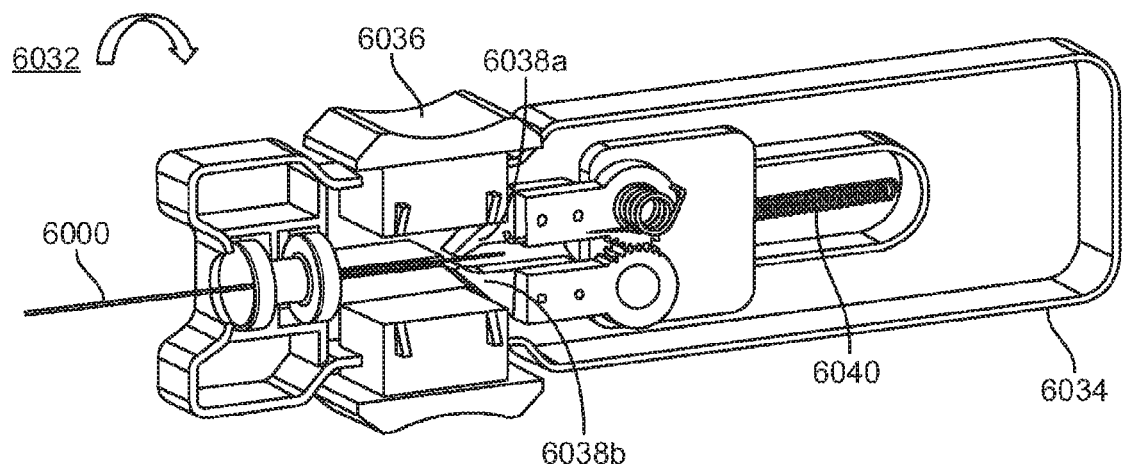

FIGS. 6A-6B show an illustration of an alternative mechanism for manually deploying an intravascular implant using a hand-held detachment device 6032. FIG. 6A shows a perspective view of a hand-held detachment device 6032 which includes a housing 6034 and an actuator switch 6036. Also shown is a primary member 6018, which in the illustrated embodiment comprises a wire, passing into the interior of the hand-held detachment device 6032. While not shown in FIGS. 6A-6B, the hand-held detachment device 6032 is located at the proximal end 2017 of detachment system is configured to allow a user to manually withdraw the primary member 6018 in a proximal direction thus deploying the implant as described. FIG. 6B shows a cross-sectional view of a hand-held detachment device 6032 which includes cam clamps 6038a and 6038b along with spring 6040. In operation, a user engages actuator 6036 which causes clamping cams 6038a and 6038b to withdraw in a proximal direction. In some embodiments of the delivery system 2000, the clamping cams grip the grip tube at the distal end 2016 of the delivery device 2000 which in these embodiments is connected to the primary member so that when the clamping cams 6038a and 6038b are withdrawn in a proximal direction the primary member is withdrawn in a proximal direction as well resulting in the tab changing from a first position to a second position as described. Spring 6040 provides resistance to prevent inadvertent activation of the clamping cams 6038a and 6038b and thus inadvertent deployment of the intravascular implant.

Figure 7:
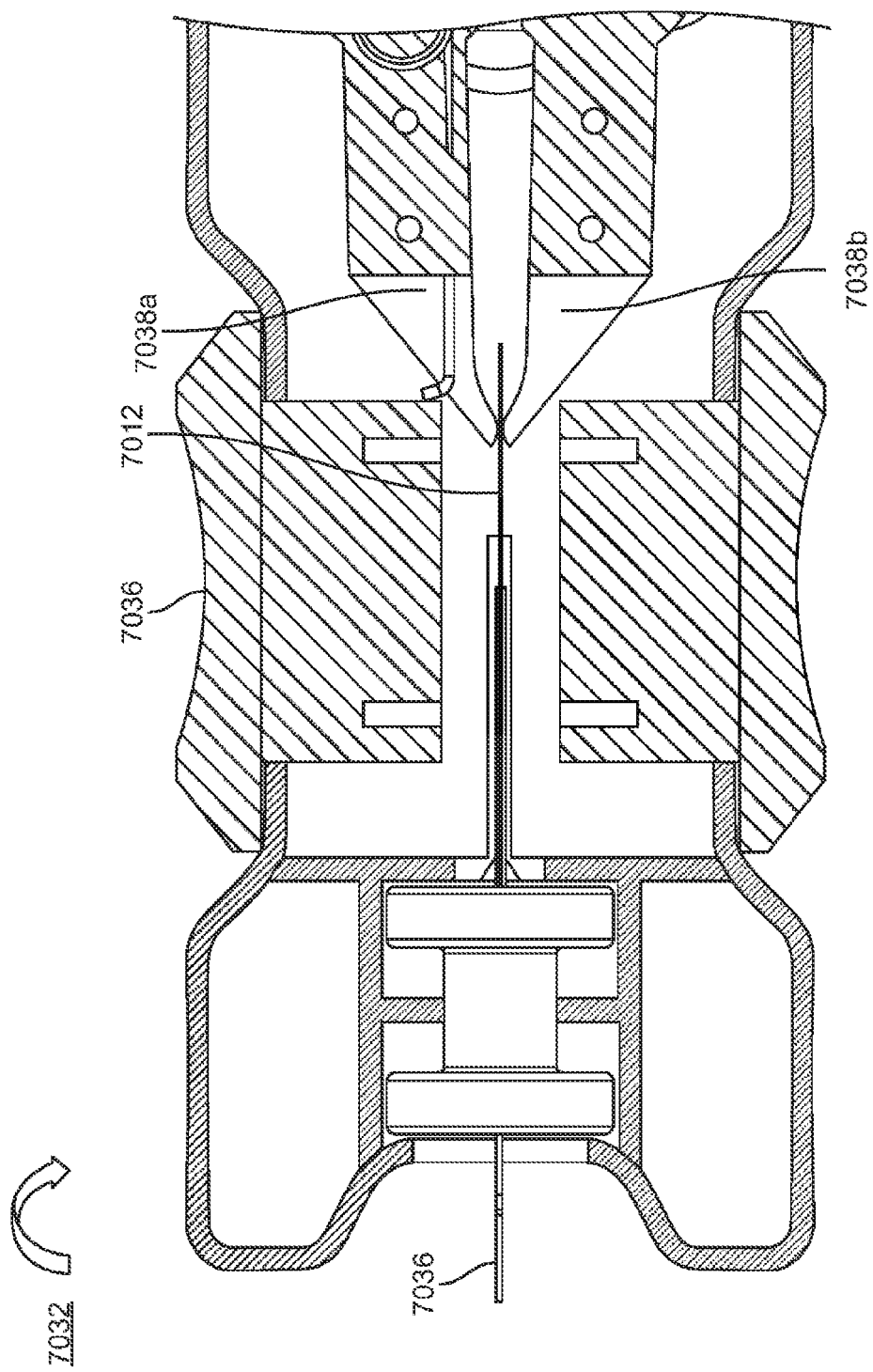
FIG. 7 shows an illustration of a close-up view of a cross-section of the hand-held detachment device which shows clamping cams griping a grip tube of the detachment system.

FIG. 7 shows an illustration of a close-up view of a cross-section of the hand-held detachment device 6032 which shows clamping cams 7038a and 7038b griping a grip tube 7012 of the delivery system 7000. Clamping cams 7038a and 7038b are activated by the actuator switch 7036, which causes proximal movement of the clamping camps 7038a and 7038b by, for example, being slid in a proximal direction by a user. In some embodiments of the hand-held detachment device 7032, the actuator switch 7036 causes the clamping cams 7038a and 7038b to both grip the grip tube 7012 and move proximally. In these embodiments, the clamping cams 7038a and 7038b only grip the grip tube 7012 when the actuator switch 7036 is engaged as a safety feature to prevent inadvertent withdrawal of the primary member.

Figure 8A:
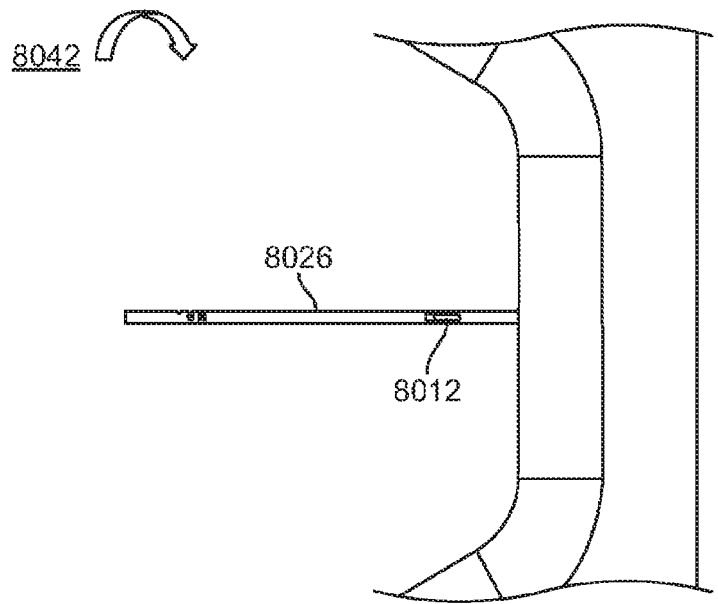
FIGS. 8A-8B show illustrations of what a user sees in a viewing window, wherein the viewing window is a feature of some embodiments of the hand-held detachment device as described.
Figure 8B:
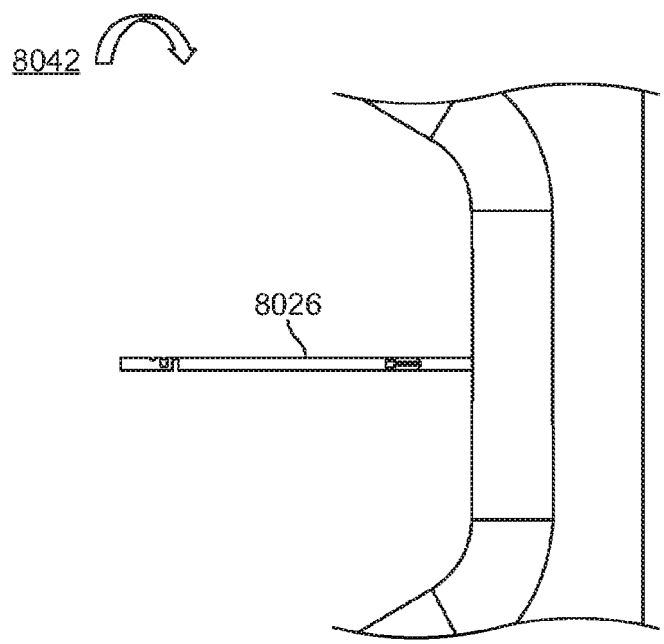

FIGS. 8A and 8B show illustrations of what a user sees in a viewing window 8042, wherein the viewing window 8042 is a feature of some embodiments of the hand-held detachment device as described. A viewing window 8042 is configured to show a user a visual confirmation that the grip tube 8012 has been withdrawn proximally by the hand-held detachment device. In FIG. 8A, a viewing window 8042 shows an expansion tube 8024 and grip tube 8012 indicating that the grip tube 8012 has not been withdrawn in a proximal direction and the primary member is therefore coupled to the tab of the detachment system. In FIG. 8B, a viewing window 8042 shows an expansion tube 8024 only indicating that the grip tube 8012 has been withdrawn in a proximal direction and the primary member is decoupled from the tab of the detachment system.

The steps of an exemplary method for deploying an intravascular implant at a target location, using any of the embodiments of the systems described herein, is as follows: Providing a user with a delivery system 2000 as shown in FIG. 2 which comprises a catheter 2002 and a detachment system 2004.

The steps of an exemplary method for deploying an intravascular implant at a target location, using any of the embodiments of the systems described herein, is as follows: Receiving a delivery system 2000 as shown in FIG. 2 which comprises a catheter 2002 and a detachment system 2004. Advancing the delivery system 2000 to an anatomical target location such as an intracranial aneurysm. Advancing the detachment system 2014 within the catheter 2002 so that the implant is advanced into the target location (i.e. the embolic coil is advanced within the aneurysm). Determining that the detachment system 2014 is in the detachment location by radiographically visualizing an alignment of an alignment of a first radiopaque marker on the catheter and a second radiopaque marker on the detachment system 2014. Alternatively or additionally, determining that the detachment system 2014 is in the detachment location by sensing a resistance to further advancement of the detachment system 2014 caused by the interlocking system coupling the catheter 2002 and the detachment system 2014 at the location of the first radiopaque marker. Alternatively or additionally, determining that the detachment system 2014 is in the detachment location by viewing the absence of a visible grip tube within a viewing window of a hand-held detachment device.

The steps of an exemplary method for deploying an intravascular implant at a target location, using any of the embodiments of the systems described herein, is as follows: Moving, by the withdrawal of a primary member from a tab of a detachment system, the tab from a first position in which it is coupled to an embolic coil or an anchoring element coupled to an embolic coil to a second position in which the tab decouples from either the embolic coil or the anchoring element thereby deploying the embolic coil.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An embolic coil delivery system for delivering and deploying an embolic coil at an aneurysm comprising:
    a conduit having a deployment location from which the embolic coil is deployed;
    a detachment system configured to fit within the conduit and to be slideably advanced and withdrawn within the conduit, the detachment system comprising:
        a housing that defines a tab, wherein the tab is configured to move from a first position to a second position, wherein when the tab is in the first position the tab is deflected toward an interior of the housing, and wherein the tab is disposed between a proximal end and a distal end of the housing;
        a primary member configured to engage the tab of the housing so that the tab is in the first position when engaged with the primary member and the tab is in the second position when the primary member is not engaged with the tab; and
        an anchoring element coupled to the embolic coil and configured to engage with the tab in the first position so that the embolic coil is coupled to the detachment system when the tab is in the first position, and wherein the anchoring element is configured to not engage with the tab in the second position so that the embolic coil is deployed when the tab is in the second position.

2. The embolic coil delivery system of claim 1, wherein the tab is integral with the housing.

3. The embolic coil delivery system of claim 1, wherein the tab rotates about a hinge.

4. The embolic coil delivery system of claim 3, wherein the hinge is parallel with an axis of the housing.

5. The embolic coil delivery system of claim 3, wherein the hinge is perpendicular with an axis of the housing.

6. The embolic coil delivery system of claim 1, wherein the tab defines a rectangular shape, wherein three edges of the tab are separated from the housing.

7. The embolic coil delivery system of claim 1, wherein the housing defines an aperture between the housing and an end portion of the tab, the end portion of the tab is opposite a hinge of the tab.

8. The embolic coil delivery system of claim 1, wherein the anchoring element is spherical.

9. An embolic coil deployment system comprising:
    an embolic coil with an anchoring element disposed at a proximal end, wherein the embolic coil is releasably coupled to a detachment mechanism via the anchoring element, the detachment mechanism comprising:
        a housing that defines a tab, wherein the tab is configured to move from a first position to a second position, wherein when the tab is in the first position the tab is deflected toward an interior of the housing and configured to engage with the anchoring element of the embolic coil to couple the embolic coil to the detachment mechanism, wherein the tab defines a rectangular shape, and wherein three edges of the tab are separated from the housing.

10. The embolic coil deployment system of claim 9, wherein when the tab is in the second position, the tab is configured to not engage with the anchoring element of the embolic coil and decouple the embolic coil from the detachment mechanism.

11. The embolic coil deployment system of claim 9, wherein the tab is disposed between a proximal end and a distal end of the housing.

12. The embolic coil deployment system of claim 9, wherein the tab rotates about a hinge.

13. The embolic coil deployment system of claim 12, wherein the hinge is parallel with an axis of the housing.

14. The embolic coil deployment system of claim 12, wherein the hinge is perpendicular with an axis of the housing.

15. The embolic coil deployment system of claim 9, wherein the system further comprises a primary member configured to engage the tab of the housing so that the tab is in the first position when engaged with the primary member and the tab is in the second position when the primary member is not engaged with the tab.

16. The embolic coil deployment system of claim 9, wherein when the tab is in the first position and directed toward the interior of the housing an end portion of the tab is disposed within the interior of the housing.

* * * * *